United States Patent [19]

Weglicki

[11] Patent Number: 5,919,828
[45] Date of Patent: Jul. 6, 1999

[54] RACEMIC PROPRANOLOL

[76] Inventor: William B. Weglicki, 8404 Coach St., Potomac, Md. 20850

[21] Appl. No.: 08/764,378

[22] Filed: Dec. 13, 1996

Related U.S. Application Data

[60] Provisional application No. 60/008,716, Dec. 15, 1995.
[51] Int. Cl.$^6$ .................................................. A61K 31/135
[52] U.S. Cl. ............................................................. 514/652
[58] Field of Search ............................................. 514/652

[56] References Cited

PUBLICATIONS

Freedman et al., Free Radical biology & Medicine (1991), 11(2), 197–206.

*Primary Examiner*—Phyllis G. Spivack
*Attorney, Agent, or Firm*—Banner & Witcoff Ltd

[57] ABSTRACT

Pharmaceutical formulations of mixtures of the D and L configuration of propranolol are disclosed that have antioxidant activity and reduced β blocking activity.

1 Claim, No Drawings

RACEMIC PROPRANOLOL

This application claims priority to provisional patent application 60/008,716 filed Dec. 15, 1995.

BACKGROUND OF THE INVENTION

1. Field of the Invention

This invention relates to formulations of pharmacologically active mixtures of D, L, propranolol and D-propranolol individually. The chemical structure of propranolol, L-[(methylethyl)amino]-3-(1-naphthalenyloxy)-2-propanol is as follows:

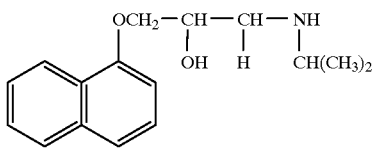

Propranolol has been commercially available for some time. It is commonly used in the treatment of hypertension, angina and arrhythmias.

2. Description of the Prior Art

α and β receptors, known as adrenoreceptors, were discovered in 1948. The β receptors are most sensitive to isoprenaline, less to epiniphrine and least to norepinephrine.

Propranolol is a well known β adrenoreceptor blocking agent, known as a β-blocker, and has the aforementioned therapeutic activities. The D and L isomers have distinct activities. The D form is known to have β blocker and antioxidant activities as reported by Mak et al. in *Free Radicals, Lipoprotein Oxidation and Artheriosclerosis* (1993) Richilieu Press, London. The D configuration is known to have antioxidant activities. Administration of β blockers may lead to harmful side effects. The acceptable dosage level of β blockers may be unpredictable with individual patients and vary widely from one patient to another.

According to the Mak et al. *Pharm. Res.* Vol. 25., No. 1 (1992) the antioxidant properties of the β blockers may have beneficial effects in the conditions commonly treated with β blockers. Commercially available propranolol, sold under many trademarks, for example INDERAL by Merck & Company, Rahwah, N.J., contains a mixture of 50% D and 50% L propranolol. Forms of pure D and pure L propranolol are not commercially available.

There is a need for a composition with both antioxidant activity and β blocking activity to provide better treatment for those conditions currently being treated by β blockers and for additional indications.

SUMMARY OF THE INVENTION

It is an object of the present invention to provide a single pharmaceutical formulation with high antioxidant properties that controls selected β blocker effects.

It is a further object of the present invention to provide a pharmaceutical composition having a large dose of d-propranolol having antioxidant properties and with a lower dosage of l-propranolol having β blocking activities.

It is a further object of the present invention to provide formulations that have different β blocker intensities and with a specific antioxidant intensity.

Formulations comprising mixtures of D and L configuration propranolol and D propranolol are disclosed.

DESCRIPTION OF THE PREFERRED EMBODIMENTS

The preparation of propranolol is described in Belgian Patents 640,312 and 640,313 as well as U.S. Pat. Nos. 3,337,628 and 3,520,919. A thorough description of the optical isomers of propranolol is found in an article by Howe and Shanks, *Nature* 210,1336 (1966). A study of the metabolism of the compound is found in an article by Bon, *Nature* 213, 721 (1967). P. A. Routledge and D. G. Shand review the pharmacokinetics of propranolol, *Appl. Pharmacokinet.* (1980), 464–485.

The present invention relates to a mixture of effective amounts of D propranolol with L propranolol so that the formulation will have antioxidant intensity in a minor effect per β blocking intensity. A preferred formulation includes a mixture of 95% D propranolol with 5% L propranolol. Both D and L propranolol have an equivalent antioxidant effect. The D propranolol has no β blocker effect where as the L propranolol does have β block intensity. Therefore, a 95:5 mixture will provide the same antioxidant intensity as pure L propranolol, but only 5% of the beta blocker effect of L propranolol. Therefore, the mixture will be equivalent to pure L propranolol, but with a 95% reduction of the β blocking affect.

Another preferred embodiment with present invention relates to a mixture of 99% D propranolol and 1% L propranolol. The 99:1 mixture is pharmacologically equivalent to pure L propranolol except that it has a 99% reduction of β blocking activity and only 1% of the β blocking intensity of L propranolol in pure form.

As stated, the percentages in the mixture of D propranolol and L propranolol may vary so there are sufficient amounts of D propranolol to lessen the β blocker affect of L propranolol.

Another embodiment of the present invention relates to a method of reducing the intensity of the β blocker effect of propranolol while maintaining the antioxidant intensity of the propranolol. This method provides a technique for reducing the intensity of the β blocking effect to the exact amount that is critical for a specific individual patient. In this method, the critical percentage reduction of β blocking effect for an individual patient is first determined. For example, it is critical for an individual patient that the propranolol have a β blocking intensity of X percent of the β blocking intensity of pure L propranolol. X may be greater than 0% and less than 100%.

A mixture of D propranolol and L propranolol is prepared when a X percent of the mixture is pure L propranolol and the 100% X of the mixture is pure D propranolol. This formulation may then be prepared by obtaining pure L propranolol and D propranolol and mixing them in the indicated percentages. This will create the exact racemic form of propranolol that is critical for the individual patient.

The same racemic mixture is critical for the patient may also be obtained by chiral separation of one configuration of L propranolol to the other configuration. For example, the commercially available propranolol, in a 50—50 mixture, or any other mixture where D propranolol and L propranolol may be subjected to chiral separation, using conventional techniques, to remove L propranolol until the resulting product for the chiral separation contains L propranolol in the reduced percentage equal to the critical percentage of β blocker intensity needed for the patient. The results in the racemic form of propranolol from the chiral separation will then have the required percentage balance between D propranolol and L propranolol, with the resulting corresponding reduction of β blocker intensity.

Compounds resulting from the mixtures of D propranolol and L propranolol and any of their pharmaceutically acceptable results are useful for the indications known for propranolol. As contemplated by this invention, the novel mixtures of the D and L propranolol can be embodied in pharmaceutical formulations wherein the adult daily dose of the D, L, configurations would range from about 50 mg. to about 500 mg. The D configuration formulation may have an adult daily dosage range of about 100 mg. to about 800 mg. with dosages adjusted to species and individual requirements. The novel mixtures of D and L propranolol of the present invention and their pharmaceutically acceptable salts can be administered orally, for example, parenterally or enternally, in convenient pharmaceutical dosage forms. For example, they can be incorporated in conventional liquid or solid vehicles such as water, gelatin, starch, magnesium stearate, talc, vegetable oils and the like to provide tablets, elixirs, capsules, solutions, emulsions and the like according to acceptable pharmaceutical practices.

Applicant, in setting forth the disclosure in the specification has cited the teaching of various articles. Such citations are meant to incorporate the teachings of these references for completeness of the disclosure.

The embodiments described herein are merely illustrative of the principles of this invention. Other arrangements and advantages may be devised by those skilled in the art without departing from the spirit and scope of the invention. Accordingly, the invention should not be deemed to be limited to the above described description, but only by the spirit of scope of the claims which follows, and their equivalents.

What is claimed is:

1. A method comprising:

a) determining for an individual patient a critical reduced percentage of β blocker intensity for pure L-propranolol, where X% is the critical reduced percentage, b) mixing a formulation of D-propranolol and L-propranolol where the mixture is 100-X% D-propranolol and X% L-propranolol, and c) Where X is greater than 0% and less than 100%.

* * * * *